(12) United States Patent
McCormick et al.

(10) Patent No.: US 11,298,484 B2
(45) Date of Patent: Apr. 12, 2022

(54) METHOD AND SYSTEMS FOR EXECUTING NASAL HIGH FLOW THERAPY WITH SETTINGS DETERMINED FROM FLOW OUTPUTS DURING A PREVIOUS VENTILATION MODE

(71) Applicant: General Electric Company, Schenectady, NY (US)

(72) Inventors: Timothy Patrick McCormick, Fitchburg, WI (US); James Hanrahan, Menomonee Falls, WI (US)

(73) Assignee: General Electric Company, Schenectady, NY (US)

( * ) Notice: Subject to any disclaimer, the term of this patent is extended or adjusted under 35 U.S.C. 154(b) by 290 days.

(21) Appl. No.: 15/979,276

(22) Filed: May 14, 2018

(65) Prior Publication Data
US 2019/0344032 A1 Nov. 14, 2019

(51) Int. Cl.
*A61M 16/00* (2006.01)
*A61M 16/06* (2006.01)
(Continued)

(52) U.S. Cl.
CPC ......... *A61M 16/0096* (2013.01); *A61B 5/087* (2013.01); *A61M 16/0057* (2013.01);
(Continued)

(58) Field of Classification Search
CPC .............. A61M 16/0096; A61M 16/01; A61M 16/021; A61M 16/022; A61M 16/024; A61M 16/026; A61M 16/0672; A61M 16/0666; A61M 16/08; A61M 16/0841; A61M 16/085; A61M 16/12; A61M 16/122; A61M 16/125; A61M 16/16;
(Continued)

(56) References Cited

U.S. PATENT DOCUMENTS

| 5,107,831 A * | 4/1992 | Halpern | A61M 16/024 |
| | | | 128/204.26 |
| 5,787,879 A * | 8/1998 | Gibson | A61M 16/08 |
| | | | 128/202.27 |

(Continued)

FOREIGN PATENT DOCUMENTS

WO  WO-2018089837 A1 *  5/2018  ............. A61H 23/04

OTHER PUBLICATIONS

Milási, C. et al., "High-flow nasal cannula: recommendations for daily practice in pediatrics," Annals of Intensive Care, vol. 4, No. 29, Sep. 30, 2014, 7 pages.

(Continued)

*Primary Examiner* — Joseph D. Boecker
*Assistant Examiner* — Brian T Khong
(74) *Attorney, Agent, or Firm* — McCoy Russell LLP

(57) ABSTRACT

Various methods and systems are provided for performing nasal high flow therapy. In one example, a method for respiratory support includes: delivering an air and oxygen mixture for nasal high flow therapy to a patient at a flow setting, the flow setting determined based on a peak inspiratory flow obtained during a previous, spontaneous breathing mode during mechanical ventilation of the patient. The flow setting may be a flow rate of a heated and humidified mixture of air and oxygen delivered via a high flow nasal cannula.

20 Claims, 5 Drawing Sheets

(51) Int. Cl.
*A61M 16/12* (2006.01)
*A61B 5/087* (2006.01)
*A61M 16/10* (2006.01)

(52) U.S. Cl.
CPC ...... *A61M 16/024* (2017.08); *A61M 16/0672* (2014.02); *A61M 16/125* (2014.02); *A61M 2016/0039* (2013.01); *A61M 2016/103* (2013.01); *A61M 2016/1025* (2013.01); *A61M 2202/0208* (2013.01); *A61M 2205/3334* (2013.01); *A61M 2210/0618* (2013.01); *A61M 2230/40* (2013.01); *A61M 2240/00* (2013.01)

(58) Field of Classification Search
CPC ............ A61M 16/161; A61M 16/0057; A61M 16/0063; A61M 16/0066; A61M 16/0069; A61M 2016/003; A61M 2016/0033; A61M 2016/0036; A61M 2016/0039; A61M 2016/0042; A61M 2016/102; A61M 2016/1025; A61M 2016/103; A61B 5/087; A61B 5/0871
See application file for complete search history.

(56) References Cited

U.S. PATENT DOCUMENTS

| | | | | |
|---|---|---|---|---|
| 6,000,396 A * | 12/1999 | Melker | ............... | A61M 16/206 128/204.21 |
| 6,390,091 B1 * | 5/2002 | Banner | ............. | A61M 16/0051 128/202.22 |
| 6,543,449 B1 * | 4/2003 | Woodring | ......... | A61M 16/0051 128/204.18 |
| 7,530,353 B2 * | 5/2009 | Choncholas | ........ | A61M 16/085 128/204.18 |
| 8,925,545 B2 * | 1/2015 | Wondka | ............ | A61M 16/0096 128/204.23 |
| 2001/0004893 A1 * | 6/2001 | Biondi | .................. | A61M 16/00 128/204.18 |
| 2003/0111078 A1 * | 6/2003 | Habashi | .............. | A61M 16/024 128/204.18 |
| 2007/0000494 A1 * | 1/2007 | Banner | .............. | G06F 19/3481 128/204.23 |
| 2008/0135044 A1 * | 6/2008 | Freitag | .................. | A61M 16/16 128/200.26 |
| 2008/0295839 A1 * | 12/2008 | Habashi | ............ | A61M 16/0069 128/204.22 |
| 2009/0229611 A1 * | 9/2009 | Martin | ................ | A61M 16/026 128/204.21 |
| 2009/0241955 A1 * | 10/2009 | Jafari | .................... | A61M 16/04 128/204.23 |
| 2009/0241958 A1 * | 10/2009 | Baker, Jr. | ............. | A61B 5/4836 128/204.23 |
| 2009/0253995 A1 * | 10/2009 | Lewis | .................... | A61B 5/087 600/538 |
| 2010/0108066 A1 * | 5/2010 | Martin | ................ | A61M 16/204 128/204.23 |
| 2011/0041849 A1 * | 2/2011 | Chen | .................. | A61B 5/14551 128/204.23 |
| 2011/0253136 A1 * | 10/2011 | Sweeney | ........... | A61M 16/0069 128/203.12 |
| 2012/0226444 A1 * | 9/2012 | Milne | ................. | A61M 16/026 702/19 |
| 2012/0291783 A1 * | 11/2012 | Peiris | .................. | A61M 16/109 128/204.21 |
| 2013/0008444 A1 * | 1/2013 | Chalvignac | ....... | A61M 16/0066 128/204.21 |
| 2013/0047990 A1 * | 2/2013 | Shelly | ................. | A61M 16/024 128/204.23 |
| 2013/0125892 A1 * | 5/2013 | Shelly | ................. | A61M 16/0875 128/204.23 |
| 2013/0133655 A1 * | 5/2013 | Kimm | ................. | A61M 16/204 128/204.23 |
| 2014/0034054 A1 * | 2/2014 | Angelico | .......... | A61M 16/0003 128/204.23 |
| 2014/0048072 A1 * | 2/2014 | Angelico | ............ | A61M 16/026 128/204.23 |
| 2014/0123979 A1 * | 5/2014 | Doyle | ............... | A61M 16/0875 128/204.23 |
| 2014/0238398 A1 * | 8/2014 | Christopher | ......... | A61B 5/4836 128/204.22 |
| 2014/0261424 A1 * | 9/2014 | Doyle | ................. | A61M 16/024 128/204.23 |
| 2014/0275901 A1 * | 9/2014 | Flanagan | ........... | A61B 5/14542 600/364 |
| 2014/0276173 A1 * | 9/2014 | Banner | ............. | A61M 16/0833 600/533 |
| 2015/0045687 A1 * | 2/2015 | Nakai | .................. | A61B 5/7246 600/533 |
| 2015/0090258 A1 * | 4/2015 | Milne | ............... | A61M 16/0069 128/202.22 |
| 2016/0166795 A1 * | 6/2016 | Belsinger, Jr. | ...... | A61M 16/205 128/203.27 |
| 2016/0193438 A1 * | 7/2016 | White | ............... | A61M 16/0003 128/203.12 |
| 2016/0287832 A1 * | 10/2016 | Cortez, Jr | ........... | A61M 16/142 |
| 2017/0239433 A1 * | 8/2017 | Martin | ................ | A61M 16/105 |
| 2017/0266399 A1 * | 9/2017 | Campana | ............... | A61B 5/486 |
| 2018/0085544 A1 * | 3/2018 | Holyoake | ............. | A61M 16/01 |
| 2018/0104426 A1 * | 4/2018 | Oldfield | ................. | A61B 5/091 |
| 2018/0126110 A1 * | 5/2018 | Payton | .............. | A61M 16/0051 |
| 2018/0236191 A1 * | 8/2018 | Martin | ............. | A61M 16/0066 |
| 2018/0280645 A1 * | 10/2018 | Lellouche | ......... | A61M 16/0003 |

OTHER PUBLICATIONS

Nishimura, M., "High-flow nasal cannula oxygen therapy in adults," Journal of Intensive Care, vol. 3, No. 1, Mar. 31, 2015, 8 pages.

* cited by examiner

METHOD AND SYSTEMS FOR EXECUTING NASAL HIGH FLOW THERAPY WITH SETTINGS DETERMINED FROM FLOW OUTPUTS DURING A PREVIOUS VENTILATION MODE

FIELD

Embodiments of the subject matter disclosed herein relate to nasal high flow therapy systems and methods for obtaining flow settings for nasal high flow therapy.

BACKGROUND

Mechanical ventilation may be used to control or support a patient's breathing. However, mechanical ventilation may be invasive and can result in patient complications. Other, less invasive, breathing therapies may be used instead of or to help transition out of mechanical ventilator support. As one example, a nasal high flow (NHF) therapy system may utilize a nasal cannula designed to administer heated and humidified air/oxygen mixtures at relatively high flows (e.g., up to 60 L/min). NHF therapy systems may increase patient comfort and tolerance as compared to traditional high-flow oxygenation systems, such as nasal masks and non-rebreathing systems. The nasal high flow therapy system reduces the chance of patient injury, achieves high $CO_2$ clearance, and reduces the entrainment of room air during patient inspiration, thereby maintaining a desired fraction of inspired oxygen ($FiO_2$) delivery. The flow setting (e.g., flow rate of delivered air/oxygen) for NHF therapy may be set to a level that achieves the desired $FiO_2$ based on a standard for an age and/or weight of the patient. In an alternate embodiment, the flow setting for NHF therapy may be set at a maximal level (e.g., 60 L/min) and then titrated down for patient comfort.

BRIEF DESCRIPTION

In one embodiment, a method for respiratory support comprises: delivering an air and oxygen mixture for nasal high flow therapy to a patient at a flow setting, the flow setting determined based on a peak inspiratory flow obtained during a previous, spontaneous breathing mode during mechanical ventilation of the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of performing nasal high flow (NHF) therapy of a patient at a flow setting obtained during mechanical ventilation of the patient. As introduced above, the flow setting (e.g., flow rate of delivered air/oxygen) for NHF therapy may be set to a level that achieves the desired $FiO_2$ based on a standard for an age and/or weight of the patient. In an alternate embodiment, the flow setting for NHF therapy may be set at a maximal level (e.g., 60 L/min) and then titrated down for patient comfort. However, the inventors herein have recognized that these methods for setting the flow rate for NHF therapy may result in an inappropriate flow rate for the patient that is either too high or too low and/or may take too much time (via trial and error) to achieve the optimal flow setting. For example, if the flow setting for NHF therapy is not high enough, room air may be entrained in the nasal prongs of the nasal cannula connected to the patient, thereby diluting the oxygen level of the delivered air/oxygen mixture and resulting in a lower than intended oxygen level being delivered to the patient (e.g., the desired $FiO_2$ may not be delivered). Alternatively, if the flow setting for NHF therapy is too high, the extra flow may create a backpressure which induces airway pressure and increases the work of breathing for the patient (e.g., results in high positive end expiratory pressure, PEEP). While a little PEEP is desired, too much PEEP may increase the patient's work of breathing due to exhaling against a higher pressure which may be uncomfortable for patients that are awake and recovering. The inventors herein have recognized the above-described issues with determining the NHF therapy flow setting. In one example, these issues may be addressed by a method for respiratory support, including: delivering an air and oxygen (air/oxygen) mixture for nasal high flow therapy to a patient at a flow setting, the flow setting determined based on a peak inspiratory flow obtained during a previous, spontaneous breathing mode during mechanical ventilation of the patient. In this way, the desired $FiO_2$ may be delivered to the patient while increasing patient comfort and reducing the time and effort to achieve the desired $FiO_2$. For example, by determining the NHF therapy flow setting based on the peak inspiratory flow obtained during mechanical ventilation, the flow setting for NHF therapy may be set slightly above the peak inspiratory demand of the patient, and thus, the desired $FiO_2$ may be delivered to the patient without inducing unnecessary PEEP.

Figure 1:
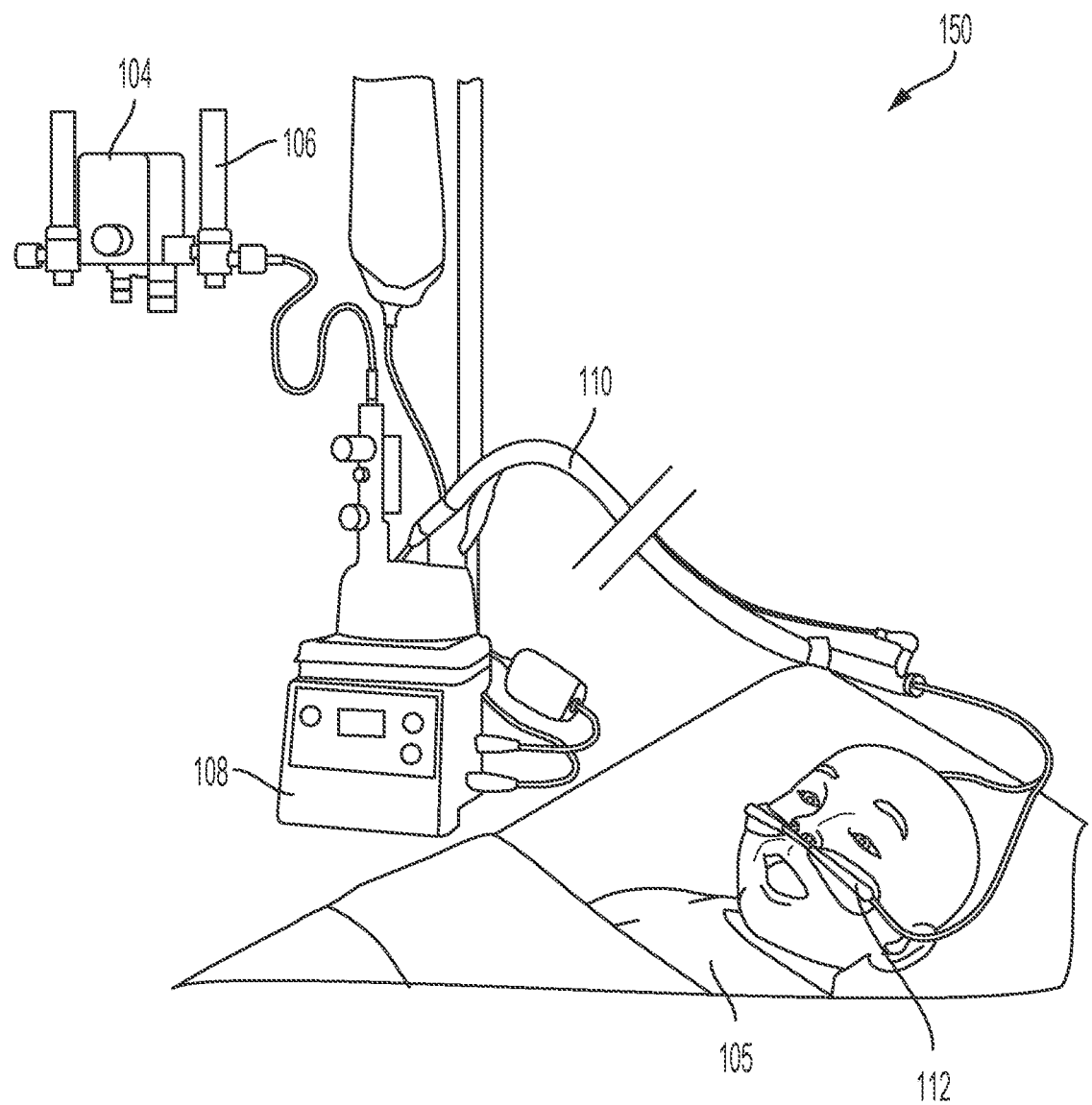
FIG. 1 shows a nasal high flow therapy system, according to an embodiment of the invention.
Figure 2:
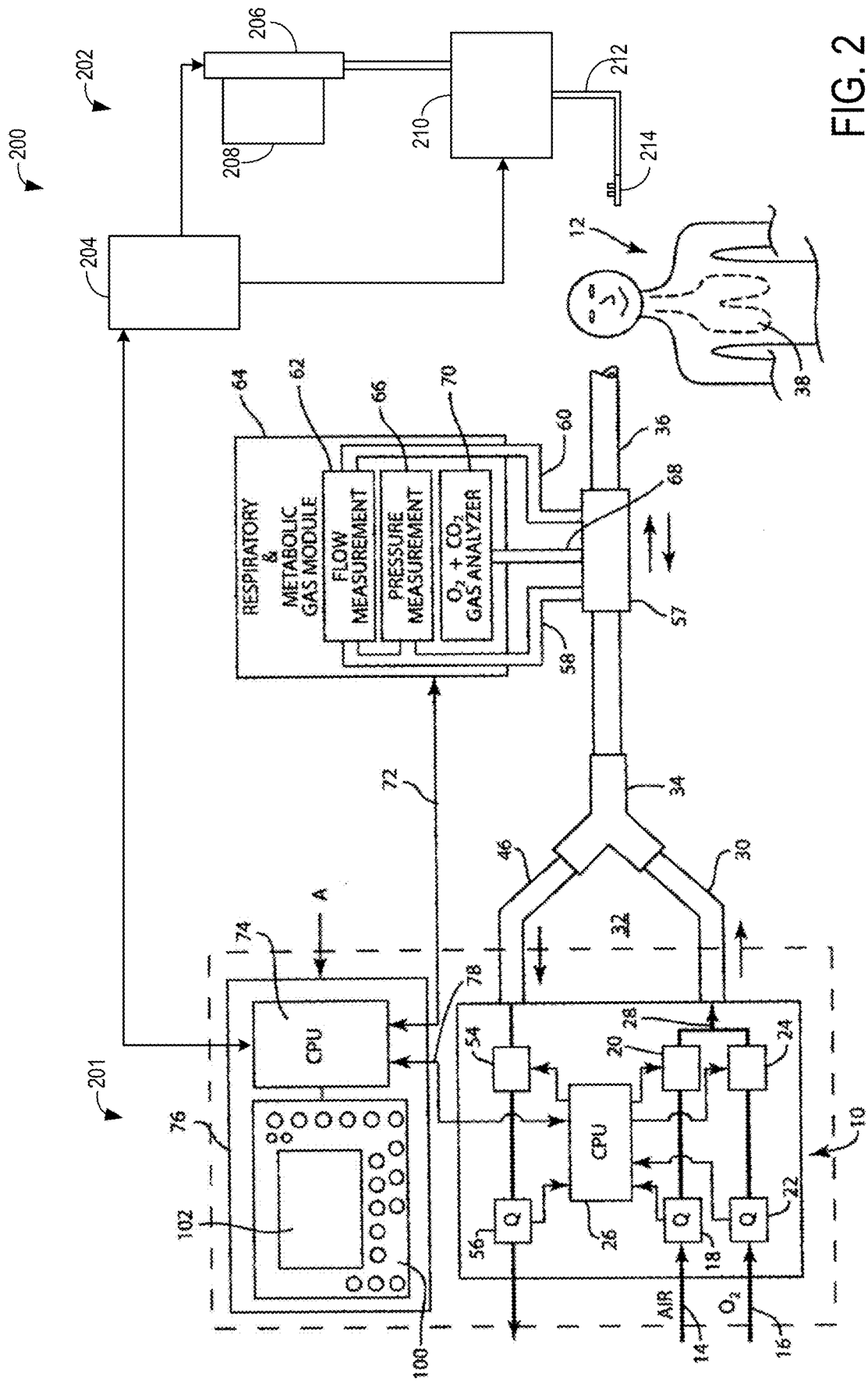
FIG. 2 shows an integrated NHF therapy and ventilator system, according to an embodiment of the invention.

Before further discussion of the approach for determining the NHF therapy flow setting based on the peak inspiratory flow obtained during mechanical ventilation, an example NHF therapy system is shown. Specifically, FIG. 1 shows an embodiment of a nasal high flow (NHF) therapy system (may also be referred to as a high-flow nasal cannula oxygen therapy system) 150 which delivers heated and humidified medical gas (e.g., an air and oxygen mixture) at relatively high flows (e.g., up to 60 L/min) to a patient 105 via a high flow nasal cannula 112. The NHF therapy system 150 includes an air/oxygen blender 104, a flow meter 106, an active heated humidifier 108, a single heated circuit 110, and the nasal cannula 112. As one example, at the air/oxygen blender 104, the inspiratory fraction of oxygen ($FIO_2$) is set from 0.21 to 1.0 in a flow of up to 60 L/min. The air-oxygen blender 104 and flow meter 106 allow for the $FIO_2$ to be adjusted independently from the flow rate. The desired flow rate for NHF therapy may be set via the flow meter 106 and/or via an electronic control unit connected to and in communication with the flow meter 106 (as shown in FIG. 2, discussed further below). As one example, in infants, the high flow rate for NHF therapy may be set at rate greater than 2 L/min or approximately 2 L/min/kg body weight. In another example, in children, the high flow rate for NHF therapy may be greater than 8 L/min.

The gas for NHF therapy is heated and humidified with the active humidifier 108 and delivered through the heated circuit 110 to the patient 105 via the nasal cannula 112. In one example, the active humidifier 108 may provide gas at a relative humidity of nearly 100% with the gas warmed to between 34° and 37° C. The nasal cannula 112 includes two prongs that are inserted into the nostrils of the patient 105. The prongs may be loose fitting so that they do not totally occlude the nostrils of the patient 105. The prongs of the nasal cannula 112 deliver the gaseous flow from the heated circuit 110 which the patient 105 inhales and the space between the outer portion of the prongs and the nostrils allows the excess inspiratory flow to vent to atmosphere and the expired gaseous flow to be vented upon exhalation.

FIG. 2 shows an integrated NHF therapy and ventilator system 200. The integrated system 200 includes a mechanical ventilation system 201 and a NHF therapy system 202. NHF therapy system 202 may be similar to and include similar components as NHF therapy system 150 shown in FIG. 1. As such, similar components to that of FIG. 1 may not be re-described below with reference to FIG. 2.

Turning to FIG. 2, mechanical ventilation system 201 includes a mechanical ventilator 10 for providing breathing gases to patient 12. Ventilator 10 receives air in conduit 14 from an appropriate source, such as a cylinder of pressurized air or a hospital air supply manifold. Ventilator 10 also receives pressurized oxygen in conduit 16, also from an appropriate source, such as a cylinder or manifold. The flow of air in ventilator 10 is measured by flow sensor 18 and controlled by valve 20. The flow of oxygen is measured by flow sensor 22 and controlled by valve 24. The operation of valves 20 and 24 is established by a control device, such as central processing unit (e.g., electronic controller, or controller) 26 in the ventilator 10.

The air and oxygen are mixed in conduit 28 of ventilator 10 and provided to inspiratory limb 30 of breathing circuit 32. Inspiratory limb 30 is connected to one arm of Y-connector 34. Another arm of Y-connector 34 is connected to patient limb 36. During inspiration, patient limb 36 provides breathing gases to lungs 38 of patient 12. Patient limb 36 receives breathing gases from the lungs of the patient during expiration. Patient limb 36 may include components such as one or more of a humidifier for the breathing gases, a heater for the breathing gases, a nebulizer, or a water trap (not shown). The breathing gases expired by patient 12 are provided through patient limb 36 and Y-connector 34 to expiratory limb 46 of breathing circuit 32. The expired breathing gases in expiratory limb 46 are provided through valve 54 and flow sensor 56 for discharge from ventilator 10. Valve 54 may be used (e.g., adjusted via one or more control or actuation signals from CPU 26) to establish the positive end expiratory pressure (PEEP) for patient 12.

Patient limb 36 includes gas flow and pressure sensor 57. While gas flow and pressure sensor 57 is depicted as a combined sensor, in alternate embodiments, the patient limb may include a separate gas flow sensor and pressure sensor. As shown in FIG. 2, a pair of pressure ports and lines 58, 60 are placed on either side of a flow restriction in the sensor and the pressure difference developed across the flow restriction is used by flow measurement unit 62 in gas module 64 to measure gas flow in patient limb 36. One of the pressure lines is connected to pressure measurement unit 66 to measure the pressure in patient limb 36. Sensor 57 also provides for a gas sampling line 68 which is connected to gas analyzer 70. Gas analyzer 70 may measure the amount of oxygen and carbon dioxide in the breathing gases. Knowing the amounts of oxygen and carbon dioxide in the breathing gases enables the amount of nitrogen to be determined as the total amount of breathing gas less the amounts of carbon dioxide and oxygen. Respiratory and metabolic gas module 64 may be a combined module for obtaining a measurement of pressure, gas composition, and gas flow (e.g., gas flow rate) of the air traveling through patient limb 36, and thus inspired and expired by the patient 12. The output of gas module 64, which may include one or more of a gas flow, gas pressure, and gas composition measurement signal, is provided in data bus 72 to central processing unit 74 in ventilator display unit 76. Central processing unit 26 in ventilator 10 is also connected to central processing unit 74 via data bus 78. As such, CPU 26 and CPU 74 are in electronic communication with one another.

Display unit 76 of ventilator 10 receives information from the ventilator 10, gas module 64, and CPU 204 (as described further below) of NHF therapy system 202 and is used by the clinician, or medical professional, to control, via data bus 78, the pneumatic control components of ventilator 10 and/or the flow and $FIO_2$ control components of NHF therapy system 202 that deliver breathing gases to patient 12. Additionally, CPU 74 in display unit 76 carries out the determination of functional residual capacity, recruited/de-recruited volumes, and other quantities employed in the present disclosure. It will be appreciated that other CPU configurations, such as a single CPU for the ventilator and its display unit, or a single CPU for the ventilator 10, display unit 76, and NHF therapy system 202, may be used, in alternate embodiments.

Ventilator display unit 76 includes user interface 100 and display 102. User interface 100 may include one or more user inputs, such as buttons, dials, toggles, key pads, switches, or the like, to input control information or commands for operating the mechanical ventilation system 201 and/or the NHF therapy system 202. The CPU 74 may receive these user inputs (e.g., commands) and then send control signals to CPU 26 and/or module 64 which may then send corresponding control signals to components of the mechanical ventilation system 201 to control mechanical ventilation of the patient 12. The CPU 74 may additionally or alternatively send control signals based on received user inputs from user interface 100 to CPU (e.g., controller) 204 of NHF therapy system 202. CPU 204 may then send corresponding control signals, such as a flow rate of an air/oxygen mixture delivered to the patient 12, a desired concentration or amount of oxygen in the air/oxygen mixture (e.g., a ratio of oxygen to total air), humidity and heat settings for the active heated humidifier 210, and the like. Display 102 may display inputted, sensed, and computed information. For example, display 102 may display several waveforms from acquired data during operation of the ventilator 10 and mechanical ventilation of the patient 12.

Figure 3:
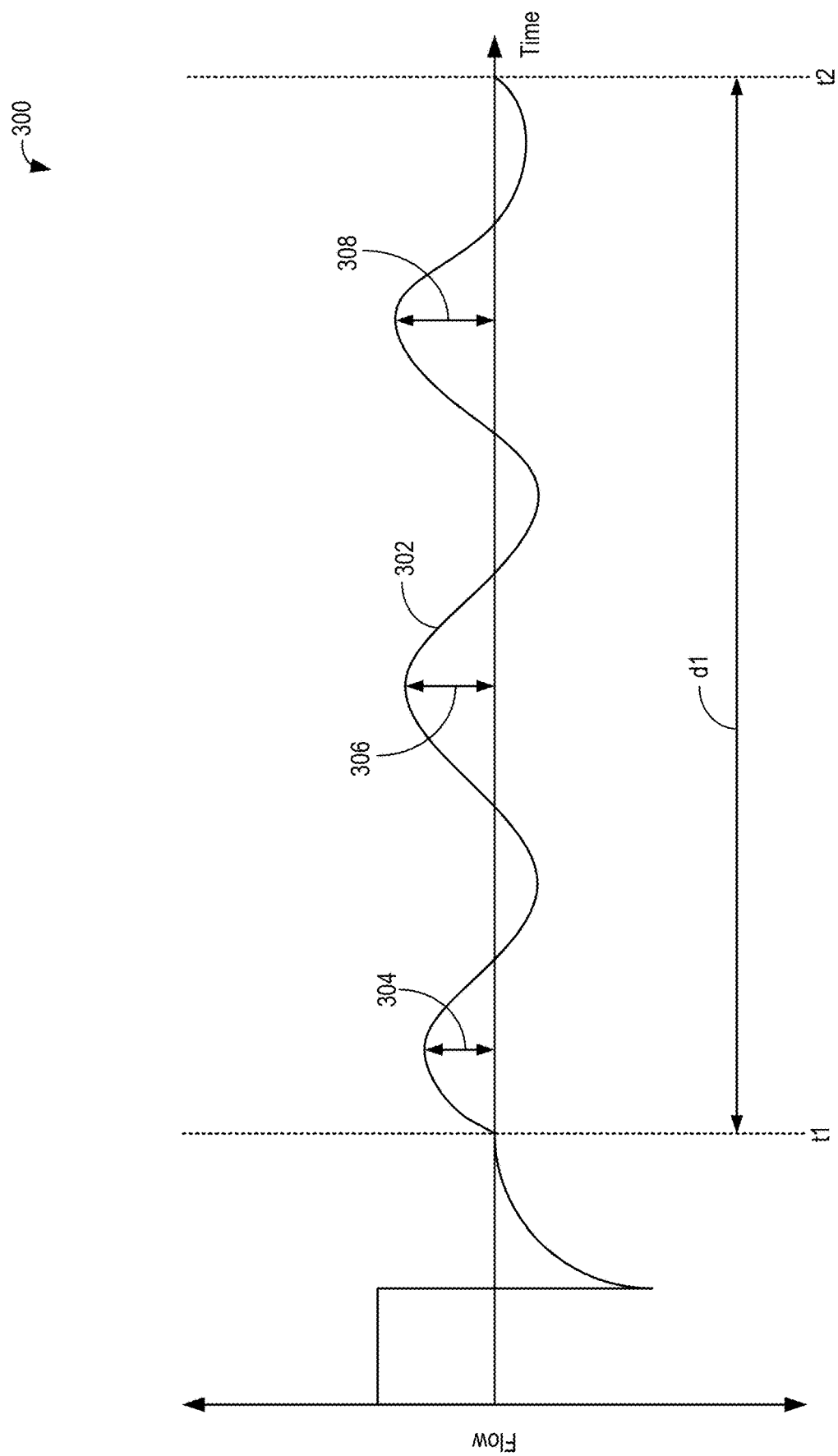
FIG. 3 shows an example flow waveform output during a spontaneous breathing mode during mechanical ventilation of a patient, according to an embodiment of the invention.

Specifically, in one embodiment, display 102 may display an airway pressure waveform, flow (e.g., flow rate) waveform, and volume waveform (all vs. time) that are generated by CPU 74 based on data or measurements acquired by module 64. An example of a flow waveform that may be generated, output, and displayed via display 102, during mechanical ventilation of the patient 12, is shown in FIG. 3, as described further below.

As introduced above, CPU 74 is also in electronic communication with CPU 204 of NHF therapy system 202. Thus, as described further below, CPU 74 (or CPU 26 if CPU 26 is electrically connected to CPU 204) may send data and/or control signals to CPU 204 for controlling NHF therapy via NHF therapy system 202. More specifically, as described further below with reference to FIGS. 3-5, CPU 74 may send peak inspiratory flow data or values obtained during certain operating modes of ventilator 10 to CPU 204 in order to set and command flow settings for NHF therapy (e.g., flow rate commands send to flow meter 206. In alternate embodiments, CPU 26 may directly communicate with CPU 204. In yet another embodiment, integrated system 200 may include one master controller that controls operation of ventilator 10, ventilator display unit 76, and NHF therapy system 202. CPU 76, CPU 26, and CPU 204 may, together, form a control system of the integrated NHF therapy and ventilator system 200.

Each of CPU 74, CPU 26, and CPU 204 may be a microcomputer, including a microprocessor unit, input/output ports, and an electronic storage medium (e.g., memory) for executable programs and calibration values. One or more of or each of CPU 74, CPU 26, and CPU 204 may be programmed with computer readable data representing instructions executable to perform the methods described below as well as other variants that are anticipated but not specifically listed. The components of mechanical ventilation system 201 and NHF therapy system 202 may be controlled at least partially by CPU 74, CPU 26, and/or CPU 204. CPUs 26, 74, and/or 204 may receive various signals from sensors of mechanical ventilation system 201 (such as flow sensors 18, 22, and 56 and gas flow and pressure sensor 57) and NHF therapy system 202, and send control signals to various actuators coupled to the ventilator 10 and/or NHF therapy system 202. The various sensors may include, for example, various temperature, pressure, and flow sensors. The various actuators may include, for example, various valves, flow meters, heaters, air/oxygen blenders, humidifiers, and the like. In one embodiment, CPU 74 and/or CPU 26 may receive flow data (during mechanical ventilation) from module 64 (or directly from sensor 57) and then process this data to output a flow waveform for display via display 102. The flow waveform data may then be sent to CPU 204 or processed at CPU 74 to determine a peak inspiratory flow for the flow waveform and flow settings for NHF therapy that is based on the peak inspiratory flow. The determined flow settings may then be turned into control signals which are sent to the flow meter 206 from CPU 204, in order to adjust the flow (e.g., a flow rate) of the air/oxygen mixture delivered to the patient 12 for NHF therapy (via inspiratory circuit 212 and nasal cannula 214) to a level corresponding to the determined flow settings.

As shown in FIG. 2, NHF therapy system 202 additionally includes flow meter 206 (similar to flow meter 106 shown in FIG. 1), air/oxygen blender 208 (similar to air/oxygen blender 104 shown in FIG. 1), active humidifier 210 (similar to humidifier 108 shown in FIG. 1), heated inspiratory circuit 212 (similar to heated inspiratory circuit 110 shown in FIG. 1), and high flow nasal cannula 214 (similar to nasal cannula 112 shown in FIG. 1). CPU 204 may be in electronic communication with, and thus send electronic control signals to, one or more or each of these components.

It should be noted that the patient 12 is not pneumatically connected to patient limb (e.g., breathing tube) 36 and nasal cannula 214 at the same time (e.g., simultaneously). Instead, the patient 12 may be connected to the ventilator via patient limb 36 during mechanical and spontaneous ventilation and then, after disconnection from patient limb 36, connected to the NHF therapy system via the nasal cannula 214.

In an alternate embodiment, the ventilator 10 may be used as the air/oxygen blender and deliver the air and oxygen mixture for NHF therapy, via the nasal cannula 214, instead of the NHF therapy system 202. In this embodiment, inspiratory circuit 212 would be connected directly to Y-connector 34 or patient limb 36. A single or dual limb breathing circuit 32 could be used; however, airway pressure (Paw) monitoring would have increased accuracy with a dual limb circuit because there would be pressure sensors at multiple locations and one or more of the pressure sensors may not be affected by pressure drop due to inspiratory flows.

In an alternate embodiment, the ventilator 10 and NHF therapy systems (e.g., NHF therapy system 202) may be separate and not integrated but may share information and/or communicate data via sending electrical signals between their respective controllers (e.g., CPU 26, CPU 76, and CPU 204) via wired or wireless (or network) connections. For example, one of the ventilator controllers may send a signal corresponding to the determined NHF therapy flow setting via a wired or network connection to the NHF therapy system controller. The NHF therapy system may then operate using the received flow setting.

FIG. 3 shows an example flow waveform that may be output and displayed during mechanical ventilation of a patient. Specifically, FIG. 3 shows a graph 300 of a flow waveform 302, with flow on the y-axis and time on the x-axis. Graph 300 may be displayed via a display (e.g., display 102 shown in FIG. 2) during mechanical ventilation of the patient. The flow waveform 302 may be generated by one or more controllers (CPUs) of the mechanical ventilation system according to flow data (e.g., measurements) received from one or more flow sensors that measure the flow of gas inspired (during inhalation) and expired (during exhalation) of the patient, while connected to the mechanical ventilator, during one or modes of mechanical ventilation. While graph 300 shows several (e.g., four) breath cycles of acquired flow data, the display may continuously display flow data as it is acquired during mechanical ventilation of the patient, and stored the flow data in a memory of the controller (CPU). In this way, the display may display real-time flow data, as it is acquired.

In the example shown by graph 300, prior to time t1, the ventilator may be operating in a volume control mechanical ventilation mode where a set volume of air is delivered to the patient via the ventilator. At time t1, in response to a request to enter a spontaneous breathing mode, the ventilator switches from the volume control mode to a spontaneous breathing mode where ventilator flow settings are adjusted so that the patient may breathe on their own, with a smaller amount of ventilator support. During the spontaneous breathing mode, the ventilator settings may be reduced to lower pressure support levels, but the patient may still be connected to the ventilator via a breathing tube. As a result, the patient may breathe, relatively, on their own and the flow waveform 302 displays those spontaneous breaths between times t1 and t2, for the duration, d1, of the spontaneous breathing mode (which may be referred to as a spontaneous breathing trial, in one example, or nasal constant positive airway pressure (nCPAP), in another example). The controller of the ventilator system and/or ventilator display unit (such as CPU 74) may determine the peak inspiratory flow of each breath cycle during the spontaneous breathing mode. As shown in graph 300, the peak inspiratory flow for each cycle during the spontaneous breathing mode, shown at 304, 306, and 308, is the positive amplitude of the flow waveform 302. Said another way, peak inspiratory flows 304, 306, and 308 are the maximum flow values during inspiration of the patient. The controller may then determine an average peak inspiratory flow value, or a highest peak inspiratory flow value, using the peak inspiratory flow value for each cycle, during the spontaneous breathing mode, that meets certain flow criteria (such as being below a maximum PEEP value, as discussed further below). In the example shown in FIG. 3, all three breath cycles occurring during the spontaneous breathing mode may meet the set flow criteria and thus, all three peak inspiratory flows 304, 306, and 308 may be averaged to determine an average peak inspiratory flow or the highest value of the three peak inspiratory flows 304, 306, and 308 may be selected during the spontaneous breathing mode during mechanical ventilation of the patient. While the average peak inspiratory flow value or highest peak inspiratory flow value is determined over duration dl, for three breath cycles, in alternate embodiments, the duration for determining the average or highest peak inspiratory flow may be longer or shorter and include more or less breath cycles. The controller may then determine a flow setting for NHF therapy, following mechanical ventilation of the patient, based on the determined average peak inspiratory flow value and/or based on the highest peak inspiratory flow (e.g., largest of peak inspiratory flows 304, 306, and 308), as described further below with reference to FIGS. 4 and 5.

Figure 4:
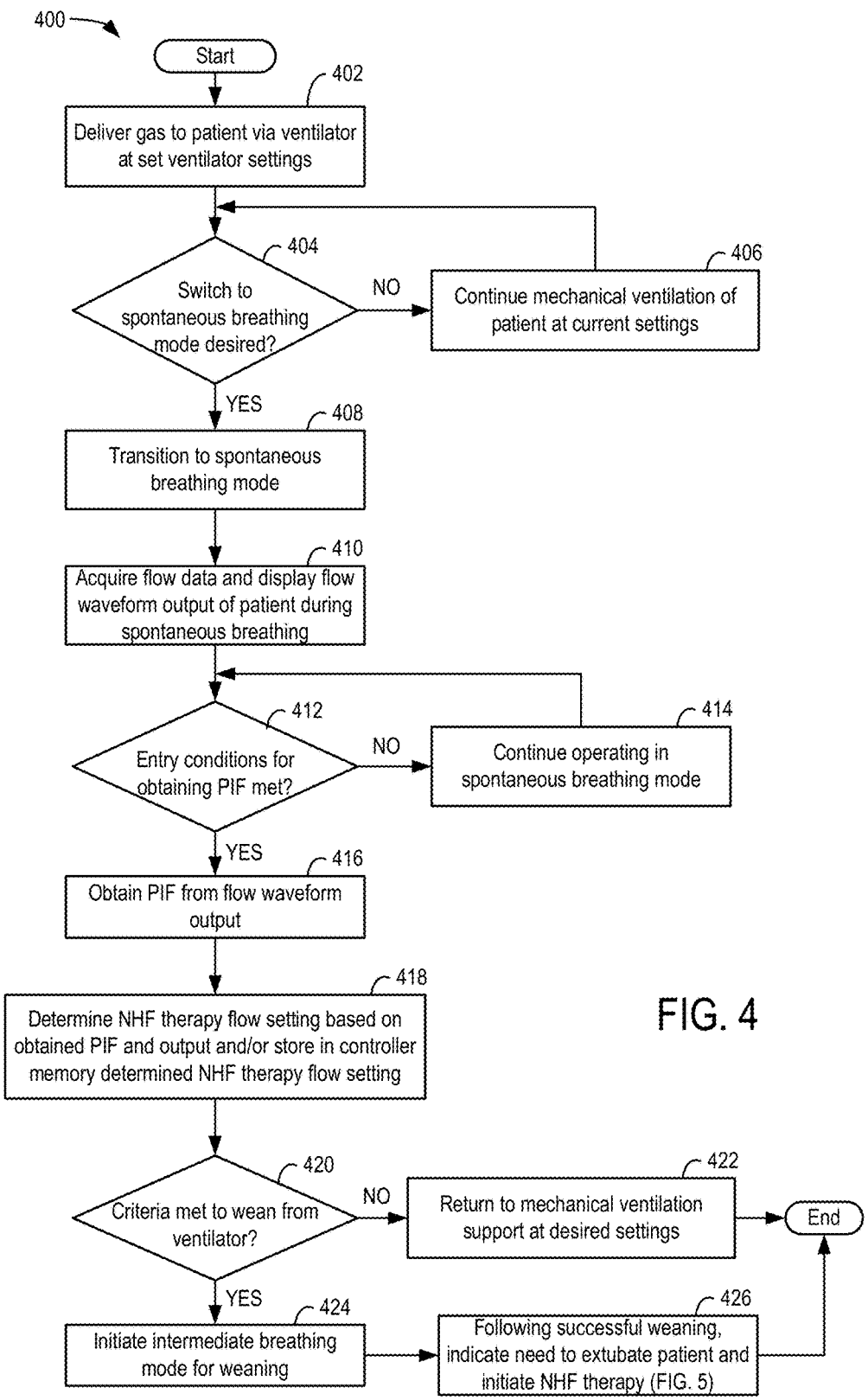
FIG. 4 shows a flow chart of a method for determining a NHF therapy flow setting during a spontaneous breathing mode during mechanical ventilation of a patient, according to an embodiment of the invention.

FIG. 4 shows a flow chart of a method 400 for determining a NHF therapy flow setting during a spontaneous breathing mode during mechanical ventilation of a patient. Instructions for carrying out method 400 and the rest of the methods included herein may be executed by one or more controllers (e.g., controllers, or CPUs, 26, 74, and/or 204 shown in FIG. 2) based on instructions stored on a memory of the one or more controllers and in conjunction with signals received from sensors of the mechanical ventilation and NHF therapy system, such as the sensors described above with reference to FIG. 2 and/or based on user inputs received via a user interface (e.g., user interface 100 shown in FIG. 2) and/or additional user inputs or controls (e.g., user controls or inputs of flow meter 206, air/oxygen blender 208, and active humidifier 210 shown in FIG. 2). The controller may employ actuators of the integrated NHF therapy and ventilation system, and/or standalone NHF therapy system and mechanical ventilation system, to adjust NHF therapy and ventilation system operation, and the delivery of gases for respiratory support to a patient, according to the methods described below.

Method 400 begins at 400 and includes delivering gas to a patient (e.g., patient 12 shown in FIG. 2) via a ventilator (e.g., ventilator 10 shown in FIG. 2, which may also be referred to as a mechanical ventilator) at set ventilator settings. In one example, this may include delivering a mixture of air and oxygen at a set ratio (or composition of air to oxygen) and at a set pressure or volume to the patient via a delivery mechanism coupled to the patient (e.g., patient limb 36 shown in FIG. 2 and an endotracheal tube coupled to the patient limb). The set ventilator settings may be received at the controller from inputs at a user input device (e.g., user interface 100 shown in FIG. 2). The method at 402 may include mechanically ventilating the patient using the mechanical ventilation system (e.g., mechanical ventilation system 201 shown in FIG. 2).

At 404, the method includes determining whether there is a request or signal to switch to a spontaneous breathing mode. For example, at 402, the ventilator may be operating in a volume or pressure control mode of mechanical ventilation where respiratory support is provided to the patient at a set volume or pressure (rather than the volume or pressure being determined "spontaneously" by the patient's own demand and breathing). Under certain conditions, such as when a user wants to test whether the ventilated patient can be weaned from the ventilator, a spontaneous breathing trial, or operating in a spontaneous breathing mode, may be requested. In one example, at 404, the controller may receive a signal, from a user input device, requesting to transition into the spontaneous breathing mode (or execute a spontaneous breathing trial). In another example, at 404, the controller may automatically determine it is time to switch to the spontaneous breathing mode based on one or more operating conditions of the ventilation system, such as a duration of mechanical ventilation, a pressure, a volume, a flow, or the like. If the controller has not received a signal or indication that a switch to the spontaneous breathing mode is desired, the method continues to 406 to continue mechanical ventilation of the patient at the current ventilator settings. Alternatively, if the controller receives a signal indicating and/or determines from ventilator operating conditions that a switch to the spontaneous breathing mode is desired, the method continues to 408.

At 408, the method includes transitioning to the spontaneous breathing mode. The method at 408 may include switching from a volume control mode (as shown in FIG. 3) or a pressure control mode of mechanical ventilation to a spontaneous breathing mode (which may also be referred to as a spontaneous breathing trial, sbt). Switching to the spontaneous breathing mode may include adjusting ventilator flow settings so that the patient may breathe on their own, with a smaller amount of ventilator support. As one example, the ventilator settings may be reduced to lower threshold levels while the patient remains connected to the breathing tube of the ventilator. As one example, a clinician may set one or more parameters for the spontaneous breathing mode including one or more main parameters including $FiO_2$, PEEP, and pressure support (PS), one or more patient synchrony parameters including inspiratory trigger, expiratory trigger, bias flow, and pressure support rise time, safety settings including peak pressure, and one or more stop criteria including respiratory rate, expired minute volume, and apnea time.

| Category | Setting |
| --- | --- |
| Main Parameters | FiO2 |
|  | PEEP |
|  | PS |
| Patient Synchrony | Insp Trigger |
|  | Exp Trigger |
|  | Bias Flow |
|  | PS Rise Time |
| Safety | Pmax |
| Stop Criteria | RR |
|  | MVexp |
|  | Apnea Time |

As a result, the patient may breathe, relatively, on their own. After the patient is breathing spontaneously, via the spontaneous breathing mode, the method continues to 410 to acquire flow data and display a flow waveform output of the patient during operation in the spontaneous breathing mode. The method at 410 may include, via the controller, acquiring pressure, volume, and flow data via one or more sensors (such as sensor 57 shown in FIG. 2) connected to the patient limb connected to the patient and processing the acquired data at one or more modules and/or controllers of the ventilation system. From the acquired data, the controller may generate a waveform (e.g., flow waveform or flow waveform output) of the inspired and expired flow of the patient vs. time. The controller may then display the generated flow waveform via a display (e.g., display 102 shown in FIG. 2). An example flow waveform generated and displayed during mechanical ventilation of the patient and during a spontaneous breathing mode is shown in FIG. 3, as described above. Method 410 may include trending the flow waveform for a preset period of time (e.g., a number of minutes or hours or number of breath cycles), or threshold duration, as explained further below.

At 412, the method includes determining whether entry conditions for obtaining a peak inspiratory flow (PIF) from the flow waveform (and acquired flow data) are met. The entry conditions may include a threshold duration of spontaneous breathing, during the spontaneous breathing mode, at a threshold positive end expiratory pressure (PEEP). For example, if PEEP is too high, the flow data acquired and output via the flow waveform may be inaccurate and may not reflect a normal, or unassisted, breathing level of the patient. Thus, flow data for determining (e.g., estimating or calculating) PIF of the flow waveform may only be obtained when PEEP is below a threshold level. In one example, the threshold level may be in the range of 0-5 cmH$_2$O. In this way, the entry conditions for obtaining the PIF from the flow waveform may be execution of the spontaneous breathing mode, at a PEEP less than the threshold PEEP level, for a threshold duration. In one example, the threshold duration may be a preset time duration or a preset number of breath cycles (where each breath cycle includes an inspiration, positive peak, and an expiration, negative peak). In another example, the entry conditions may additionally or alternatively include completion of a successful spontaneous breathing trial, which may be defined as no apnea, expired minute volume, or respiratory rate alarms occurring during the trial. If the entry conditions for obtaining the PIF are not met, the method continues to 414 to continue operating in the spontaneous breathing mode and continue acquiring flow data and displaying the flow waveform via the display.

Alternatively at 412, if the entry conditions for obtaining the PIF from the flow waveform are met, the method continues to 416 where the method includes obtaining the PIF from the flow waveform output (or the flow data that the waveform output is generated from). The method at 416 may include determining which breath cycles meet the entry criteria, and then determining the PIF for each breath cycle that meets the entry criteria, for the threshold duration. As explained below, the threshold duration may be a threshold amount of time or number of breath cycles. As one example, the PIF may be determined from a preset number of breath cycles, such as eight breaths. The controller may then determine the PIF, from the flow waveform and corresponding flow data (e.g., flow rate greater than 2 L/min) for each of the eight breath cycles that meet the entry criteria. As explained above with reference to FIG. 3, determining the PIF for a breath cycle may include determining the peak flow value for that breath, which may be the positive amplitude of the flow waveform or the maximum flow value during inspiration of the patient. The controller may then average each PIF value for each of the eight (or however many are in the preset threshold duration) breath cycles to determine an average PIF value. In alternate embodiments, instead of averaging each PIF value, the method at 416 may include obtaining the highest PIF value for each of the breath cycles or obtaining the most prevalent or median PIF value out of all the breath cycles in the threshold duration or number of breath cycles.

At 418, the method includes determining a NHF therapy flow setting based on the obtained PIF flow and then outputting and/or storing in the memory of the controller the determined NHF therapy flow setting. In one example, the method at 418 may include determining the NHF therapy flow setting based on the average PIF value determined at 416. For example, the controller may determine the NHF therapy setting to be the value of the determined average PIF. In another example, the controller may determine the NHF therapy setting to be a function of the determined average PIF. For example, the NHF therapy setting may be determined by multiplying the average PIF value by a constant value (such as 1.2). In this way, the NHF therapy setting may be directly proportional to the determined PIF. For example, the NHF therapy setting may be at least as large as the average PIF. Thus, the controller may determine the NHF therapy flow setting according to a function or look-up table stored in memory of the controller. As one example, the average PIF (or alternate PIF value determined at 416, such as the maximum PIF or median PIF) may be the input to the stored look-up table and the NHF therapy flow setting (e.g., flow rate, in units of L/min, in one example) may be the output from the table. The determined NHF therapy flow setting may then be stored within the memory of the controller until it is requested. In another example, the determined NHF therapy flow setting may be output and displayed via the user interface display (e.g., display 102 shown in FIG. 2). In this way, a user (e.g., doctor, nurse, or technician) may obtain the NHF therapy flow setting and input the obtained NHF therapy flow setting into the NHF therapy system during, or before starting, NHF therapy of the patient (e.g., the same patient that was mechanically ventilated and underwent the spontaneous breathing trial or mode prior to NHF therapy).

At 420, the method includes determining whether criteria is met for weaning the patient from the ventilator. As one example, criteria for weaning the patient from the ventilator may be a request to wean the patient (via a user input received at the controller), a successful or completion of a spontaneous breathing trial, threshold settings (e.g., pressure, volume, and/or flow) being met during the spontaneous breathing mode of the patient, or the like. If it is determined that the patient does not meet criteria for weaning, or weaning of the patient from the ventilator is not desired or requested via the user/operator, the method continues to 422 to return to one of the other mechanical ventilation modes (e.g., pressure or volume support) at the desired or set/commanded settings. The method then ends. Alternatively, if the criteria for weaning the patient from the ventilator is met, the method continues to 424 to initiate an intermediate breathing mode for weaning the patient from the ventilator. In one example, the intermediate breathing mode may include one or more of a continuous positive airway pressure (CPAP) mode and/or a nasal continuous positive airway pressure (NCPAP) mode. In alternate embodiments, there may be no intermediate mode for weaning the patient from the ventilator. The method then continues to 426 where, following successful weaning of the patient from the mechanical ventilator, the method includes indicating a need to extubate the patient and initiate NHF therapy (as detailed in FIG. 5, described further below). The method at 426 may additionally or alternately include stopping ventilator support in response to a shut-down (or power off) signal which may be received at the controller from a user interface or power switch. The method then ends.

In alternate embodiments, instead of determining a PIF value for determining the NHF therapy setting during a spontaneous breathing mode, as explained above, the PIF may be measured and trended during one of the above-described intermediate breathing modes to determine the NHF therapy setting. For example, during an intermediate breathing mode (e.g., CPAP mode), the PIF may be determined from a patient breathing waveform, similarly to as described above during the spontaneous breathing mode, and then used to determine the NHF therapy setting (as described at 418).

Figure 5:
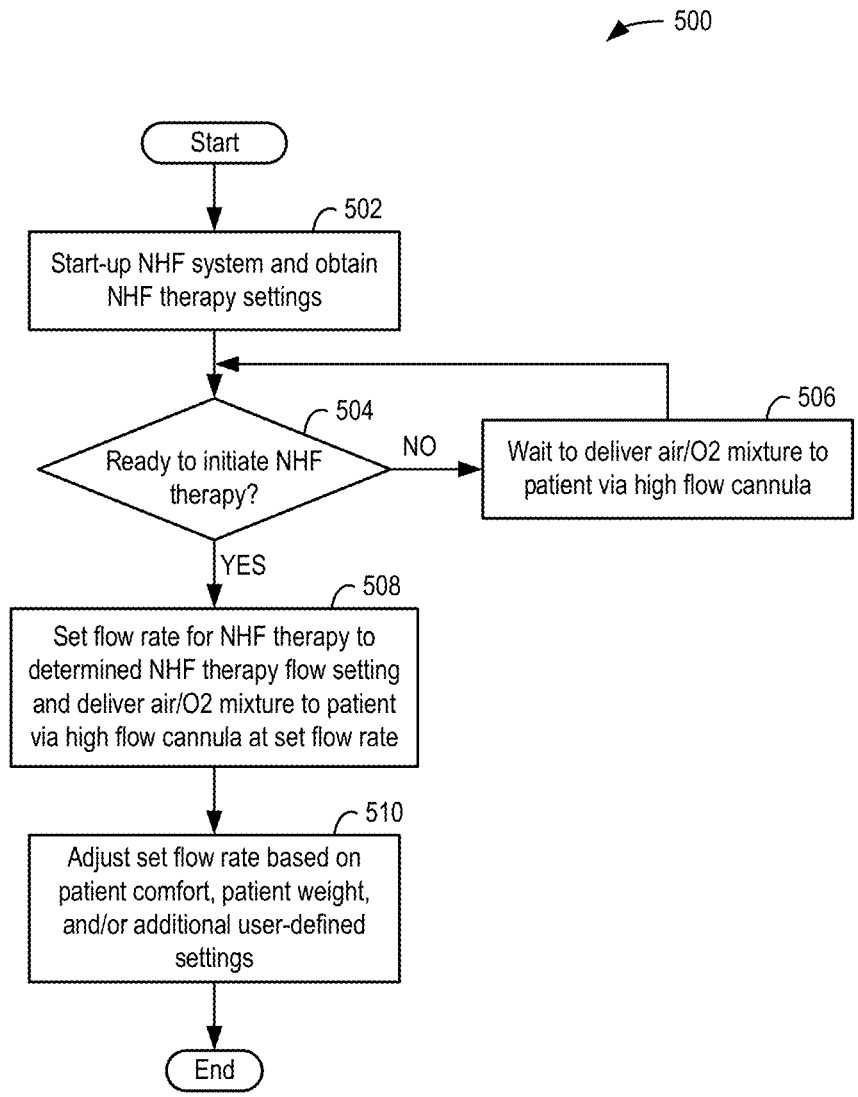
FIG. 5 shows a flow chart of a method for performing NHF therapy using a flow setting obtained during mechanical ventilation of the patient, according to an embodiment of the invention.

FIG. 5 shows a flow chart of a method 500 for performing NHF therapy using a flow setting obtained during mechanical ventilation of the patient. In one embodiment, method 500 may continue directly from method 400. In another embodiment, method 500 may be initiated upon start-up or initialization of a NHF therapy system (such as NHF therapy system 150 shown in FIG. 1 or NHF therapy system 202 shown in FIG. 2). Method 500 may be executed by a controller of the NHF therapy system (such as controller 204 shown in FIG. 2). In one embodiment, the NHF therapy system may be a standalone system that receives flow settings for NHF therapy via user inputs at one or more components of the NHF therapy system (e.g., air/oxygen blender 104, flow meter 106, and/or active heated humidifier 108 shown in FIG. 1), or a controller of the NHF therapy system (e.g., controller 204). In another embodiment, the NHF therapy system may be included within an integrated NHF therapy and ventilator system (e.g., integrated NHF therapy and ventilator system 200 shown in FIG. 2). In this embodiment, method 500 may be executed by one or more of a controller of the NHF therapy portion of the integrated system (e.g., CPU 204), a controller of a display unit 76 (e.g., CPU 74), a controller of the ventilator portion of the system (e.g., CPU 26), and/or a common controller to the entire integrated system.

Method 500 begins at 502 by starting up (e.g., powering on) the NHF therapy system and obtaining NHF therapy settings. In one embodiment, starting up the NHF therapy system may include powering on the electrical components of the NHF therapy system (such as the air/oxygen blender, flow meter, humidifier, and heated circuit) in response to a start-up signal from a user (e.g., generated upon actuation of a power switch or button). In another embodiment, starting up of the NHF therapy system may be executed by one or more controllers of the integrated system in response to a signal generated from the one or more controllers (such as a CPU electrically connected to the ventilator portion of the integrated system) indicating that the patient has been weaned from the mechanical ventilator and NHF therapy should be executed. The NHF therapy settings obtained at 502 may include one or more flow settings (e.g., flow rate), which was determined during mechanical ventilation of the patient, as explained above with reference to FIG. 5, a $FiO_2$ level for the air/oxygen blender, an initial setting for the humidifier (e.g., humidity percentage or level), and/or a temperature setting for the heated circuit. One or more of the NHF therapy settings may be automatically obtained at the controller of the NHF therapy system via one or more controllers of the integrated NHF therapy and ventilator system. Additionally or alternatively, one or more of the NHF therapy settings may be obtained via user inputs at one or more of the controller, air/oxygen blender, flow meter, humidifier, and heated circuit of the NHF therapy system.

At 504, the method includes determining whether the user/operator and/or the system is ready to initiate NHF therapy. In one example, the controller or components of the NHF therapy system may receive a user input or user-initiated signal indicating it is time to initiate NHF therapy. If it is not time to initiate NHF therapy, the method continues to 506 to wait to deliver the air/oxygen mixture to the patient via the high flow nasal cannula of the NHF therapy system. However, if initiating NHF therapy is requested, the method continues to 508 to set the flow rate (e.g., at the flow meter) for NHF therapy to the determined NHF therapy setting and deliver the air/oxygen mixture to the patient via the high flow nasal cannula at the set flow rate (and at any other NHF therapy settings designated at 502). In one embodiment, the method at 508 may include automatically looking up the determined NHF therapy flow setting stored in the controller (e.g., the flow setting determined and stored at 418 in FIG. 4) and automatically setting the flow rate for NHF therapy (e.g., the flow rate of the air/oxygen mixture delivered to the patient via the high flow cannula) at the determined flow setting. This may include the controller sending a control signal to an actuator of the flow meter of the NHF therapy system to adjust the flow rate to the determined NHF therapy flow setting. In another embodiment, the method at 508 may include receiving a user input of the determined NHF therapy flow setting that was output (e.g., via a display) to the user during the spontaneous breathing mode during mechanical ventilation of the patient. In this way, the user may manually input the determined NHF therapy setting at the flow meter (e.g., via a knob or button) or at a user input device coupled with the controller. The method then continues to 510 to adjust the set flow rate based on one or more of patient comfort, patient weight, and/or additional user defined settings. For example, after a duration of delivering the air/oxygen mixture for NHF therapy to the patient at the flow setting determined during the spontaneous breathing mode during mechanical ventilation of the patient, a user may manually adjust (via a user input at the flow meter or alternate user input device) the flow rate (e.g., increase or decrease) to a level that increases the comfort of the patient. In another example, the controller may automatically adjust the set flow rate based on the patient's weight, if the flow setting determined during mechanical ventilation is a threshold amount different than an estimated flow rate for NHF therapy determined based on the patient's weight alone (and not based on the PIF during the spontaneous breathing mode).

In this way, the flow settings for NHF therapy may be learned and determined during a spontaneous breathing mode during mechanical ventilation of a patient. As explained above, during mechanical ventilation, a spontaneous breathing mode (or spontaneous breathing trial) may be executed where the patient breathes relatively on their own while flow data is acquired. This acquired flow data may be displayed in the form of a flow waveform and then a peak inspiratory flow or average peak inspiratory flow for a number (e.g., greater than one) of breath cycles of the flow waveform may be determined. The peak inspiratory flow may then be used to determine the flow setting (e.g., flow rate), which may be an initial flow setting, for NHF therapy that follows the spontaneous breathing mode, after the patient has been weaned from the ventilator. As explained above, a NHF therapy flow rate that is too high may create backpressure which increases the breathing work for the patient (which is not comfortable for awake and recovering patients). At the same time, a NHF therapy flow rate that is too low may result in the entrainment of room air in the nasal prongs of the high flow cannula, which may dilute the oxygen level, thereby resulting in the patient not getting the desired $FiO_2$ level. The technical effect of delivering the air/oxygen mixture for nasal high flow therapy to a patient at a flow setting, the flow setting determined based on a peak inspiratory flow obtained during a spontaneous breathing mode during mechanical ventilation of the patient is to more easily obtain an accurate (e.g., optimum) NHF therapy flow setting that increases patient comfort and reduces patient breathing work while delivering a desired $FiO_2$ level. This method also reduces the time it takes to determine the correct NHF therapy flow setting via trial and error (or titrating down from a maximal, or upper threshold level, such as 60 L/min). As a result, a care provider may save time and effort in finding the correct, or ideal, flow setting for NHF therapy.

As one embodiment, a method for respiratory support, comprises: delivering an air and oxygen mixture for nasal high flow therapy to a patient at a flow setting, the flow setting determined based on a peak inspiratory flow obtained during a previous, spontaneous breathing mode during mechanical ventilation of the patient. As one example, the delivering the air and oxygen mixture for nasal high flow therapy at the flow setting occurs immediately following the spontaneous breathing mode, without additional flow modes occurring between the spontaneous breathing mode and the nasal high flow therapy. As another example, the delivering the air and oxygen mixture for nasal high flow therapy at the flow setting occurs immediately following an intermediate breathing mode which occurs immediately following the spontaneous breathing mode, where the intermediate breathing mode includes one of a continuous positive airway pressure mode and a nasal continuous positive airway pressure mode. In one example of the method, the flow setting is an initial flow rate of the air and oxygen mixture flowing to the patient from a nasal high flow therapy system. The method may further comprise adjusting the initial flow rate based on one or more of patient weight and patient comfort. In another example of the method, delivering the air and oxygen mixture for nasal high flow therapy includes delivering the air and oxygen mixture to the patient via a high flow nasal cannula. The method may further comprise, via a controller, automatically obtaining the peak inspiratory flow from a waveform output produced during the spontaneous breathing mode during mechanical ventilation of the patient, automatically determining the flow setting based on the automatically obtained peak inspiratory flow, and, upon transitioning from mechanical ventilation to nasal high flow therapy, delivering the air and oxygen mixture for nasal high flow therapy to the patient at the automatically determined flow setting. In one example, the controller is in electronic communication with each of a mechanical ventilator and a nasal high flow therapy system. The method may further comprise automatically obtaining the peak inspiratory flow from a waveform output produced during the spontaneous breathing mode during mechanical ventilation of the patient, in response to spontaneous breathing of the patient, during the spontaneous breathing mode, for a threshold duration below a threshold positive end expiratory pressure. In one example, automatically obtaining the peak inspiratory flow from the waveform output includes averaging the peak inspiratory flow of the waveform output over a predetermined period of time during the spontaneous breathing mode.

As another embodiment, a method for respiratory support, comprises: while operating a respiratory support device, attached to a patient, in a spontaneous breathing mode during mechanical ventilation of the patient, displaying a breathing waveform of the patient and obtaining a peak inspiratory flow from the breathing waveform; and following the spontaneous breathing mode and after stopping mechanical ventilation of the patient, delivering an air and oxygen mixture via a nasal high flow therapy system to the patient at a flow rate that is determined based on the peak inspiratory flow. The method may further comprise automatically determining the flow rate via a controller in electronic communication with a controller of the respiratory support device and a flow meter of the nasal high flow therapy system. In one example, automatically determining the flow rate includes trending the breathing waveform over a predetermined period of time, during the spontaneous breathing mode, and averaging peak inspiratory flow measurements for each breath cycle of the trended breathing waveform over the predetermined period of time to obtain an average peak inspiratory flow. The method may further comprise setting the flow rate for nasal high flow therapy at a level that is a function of the average peak inspiratory flow. In another example, the method may further comprise starting the predetermined period of time for trending the breathing waveform only after positive end expiratory pressure is below a threshold level. In yet another example, the spontaneous breathing mode is a spontaneous breathing trial and further comprising determining the flow rate for nasal high flow therapy based on the peak inspiratory flow in response to conclusion of the spontaneous breathing trial and a request to wean the patient from mechanical ventilation.

As yet another embodiment, a system, comprises: a mechanical ventilator adapted to provide respiratory support to a patient; and a control system with one or more controllers with computer readable instructions stored on non-transitory memory that when executed during operation of the mechanical ventilator, cause the one or more controllers to: execute a spontaneous breathing mode in response to a request for the spontaneous breathing mode; during executing of the spontaneous breathing mode, acquire flow data from a plurality of breath cycles; and determine a nasal high flow therapy flow setting based on a peak inspiratory flow of the acquired flow data. The system may further comprise a user interface with a display and the computer readable instructions may further cause the one or more controllers to display a flow waveform of the acquired flow data and the determined nasal high flow therapy via the display. In one embodiment, the system further comprises a nasal high flow therapy system including a high flow cannula adapted to deliver an air and oxygen mixture to the patient and the one or more controllers include computer readable instructions that when executed during operation of the nasal high flow therapy system, cause the one or more controllers to deliver the air and oxygen mixture for nasal high flow therapy to the patient, via the high flow cannula, at the determined nasal high flow therapy setting. In another example, the nasal high flow therapy system includes a humidifier and heated circuit coupled with the high flow cannula and wherein the air and oxygen mixture delivered to the patient is a heated and humidified air and oxygen mixture.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for respiratory support, comprising:
delivering an air and oxygen mixture for nasal high flow therapy to a patient at a flow setting, the flow setting determined via a controller coupled to a ventilator, based on a peak inspiratory flow obtained during a previous, spontaneous breathing mode during invasive mechanical ventilation of the patient with the ventilator, wherein the invasive mechanical ventilation is a different mechanical ventilation than the nasal high flow therapy; and
wherein the air and oxygen mixture of the nasal high flow therapy and the air and oxygen mixture of the ventilator are from a same source.

2. The method of claim 1, wherein the delivering the air and oxygen mixture for nasal high flow therapy at the flow setting occurs immediately following the previous, spontaneous breathing mode, without additional flow modes occurring between the previous, spontaneous breathing mode and the nasal high flow therapy.

3. The method of claim 1, wherein the delivering the air and oxygen mixture for nasal high flow therapy at the flow setting occurs immediately following an intermediate breathing mode which occurs immediately following the previous, spontaneous breathing mode, where the intermediate breathing mode includes one of a continuous positive airway pressure mode via an invasive mechanical ventilator and a nasal continuous positive airway pressure mode.

4. The method of claim 1, wherein the flow setting is an initial flow rate of the air and oxygen mixture flowing to the patient from a nasal high flow therapy system.

5. The method of claim 4, further comprising adjusting the initial flow rate based on one or more of patient weight and patient comfort.

6. The method of claim 1, wherein the delivering the air and oxygen mixture for nasal high flow therapy includes delivering the air and oxygen mixture to the patient via a high flow nasal cannula.

7. The method of claim 1, further comprising, via the controller, automatically obtaining the peak inspiratory flow from a waveform output produced during the previous, spontaneous breathing mode during the invasive mechanical ventilation of the patient, automatically determining the flow setting based on the automatically obtained peak inspiratory flow, and, upon transitioning from the invasive mechanical ventilation to the nasal high flow therapy, delivering the air and oxygen mixture for the nasal high flow therapy to the patient at the automatically determined flow setting.

8. The method of claim 7, wherein the controller is in electronic communication with each of an invasive mechanical ventilator and a nasal high flow therapy system.

9. The method of claim 1, further comprising automatically obtaining, via the controller, the peak inspiratory flow from a waveform output produced during the spontaneous breathing mode during the invasive mechanical ventilation of the patient, in response to spontaneous breathing of the patient, during the spontaneous breathing mode, for a threshold duration below a threshold positive end expiratory pressure.

10. The method of claim 9, wherein automatically obtaining the peak inspiratory flow from the waveform output includes averaging the peak inspiratory flow of the waveform output over a predetermined period of time during the spontaneous breathing mode.

11. A method for respiratory support, comprising:
while operating a respiratory support device, attached to a patient, in a spontaneous breathing mode during invasive mechanical ventilation of the patient, displaying a breathing waveform of the patient, and, in response to successful completion of a spontaneous breathing trial, obtaining a peak inspiratory flow from the breathing waveform; and
following the spontaneous breathing mode and after stopping the invasive mechanical ventilation of the patient, delivering an air and oxygen mixture via a nasal high flow therapy system to the patient at a flow rate, wherein the flow rate at start-up of nasal high flow therapy is determined based on the peak inspiratory flow,
wherein the invasive mechanical ventilation is a different mechanical ventilation than the nasal high flow therapy.

12. The method of claim 11, further comprising automatically determining the flow rate via a controller in electronic communication with a controller of the respiratory support device and a flow meter of the nasal high flow therapy system, wherein the successful completion of the spontaneous breathing trial is based on an absence of any of apnea, expired minute volume, or respiratory rate alarms occurring during the spontaneous breathing trial.

13. The method of claim 12, wherein automatically determining the flow rate includes trending the breathing waveform over a predetermined period of time, during the spontaneous breathing mode, and averaging peak inspiratory flow measurements for each breath cycle of the trended breathing waveform over the predetermined period of time to obtain an average peak inspiratory flow.

14. The method of claim 13, further comprising setting the flow rate for nasal high flow therapy at a level that is a function of the average peak inspiratory flow.

15. The method of claim 13, further comprising starting the predetermined period of time for trending the breathing waveform only after positive end expiratory pressure is below a threshold level.

16. The method of claim 11, further comprising determining the flow rate for nasal high flow therapy based on the peak inspiratory flow in response to conclusion of the spontaneous breathing trial and a request to wean the patient from the invasive mechanical ventilation.

17. A system, comprising:
a nasal high flow therapy system;
an invasive mechanical ventilator adapted to provide respiratory support to a patient, wherein the invasive mechanical ventilator is a different respiratory support than the nasal high flow therapy; and
a control system with one or more controllers with computer readable instructions stored on non-transitory memory that, when executed during operation of the invasive mechanical ventilator, cause the one or more controllers to:
execute a spontaneous breathing mode in response to a request for the spontaneous breathing mode;
during execution of the spontaneous breathing mode during the invasive mechanical ventilation, acquire flow data from a plurality of breath cycles; and
determine a nasal high flow therapy flow setting based on a peak inspiratory flow of the acquired flow data.

18. The system of claim 17, further comprising a user interface with a display, wherein the computer readable instructions further cause the one or more controllers to display a flow waveform of the acquired flow data and the determined nasal high flow therapy flow setting via the display.

19. The system of claim 17, further comprising a nasal high flow therapy system including a high flow cannula adapted to deliver an air and oxygen mixture to the patient, wherein the one or more controllers include computer readable instructions that, when executed during operation of the nasal high flow therapy system, cause the one or more controllers to deliver the air and oxygen mixture for nasal high flow therapy to the patient, via the high flow cannula, at the determined nasal high flow therapy flow setting.

20. The system of claim 19, wherein the nasal high flow therapy system includes a humidifier and a heated circuit coupled with the high flow cannula and wherein the air and oxygen mixture delivered to the patient is a heated and humidified air and oxygen mixture.

* * * * *